United States Patent
Rupp et al.

(10) Patent No.: US 7,134,216 B2
(45) Date of Patent: Nov. 14, 2006

(54) DEVICE FOR LENGTH AND DEPTH MEASUREMENTS IN SURGERY

(75) Inventors: Stephan Rupp, Küblis (CH); Jörg Peltzer, Delémont (CH)

(73) Assignee: Synthes (USA), West Chester, PA (US)

( * ) Notice: Subject to any disclaimer, the term of this patent is extended or adjusted under 35 U.S.C. 154(b) by 0 days.

(21) Appl. No.: 10/910,750

(22) Filed: Aug. 3, 2004

(65) Prior Publication Data

US 2005/0066535 A1  Mar. 31, 2005

Related U.S. Application Data

(63) Continuation of application No. PCT/CH02/00071, filed on Feb. 7, 2002.

(51) Int. Cl.
*A61B 1/00* (2006.01)
*A61F 5/04* (2006.01)

(52) U.S. Cl. ............................ 33/512; 33/542; 33/810; 606/102

(58) Field of Classification Search .......... 33/511–512, 33/542, 836, 810–812; 606/78, 86, 102–103, 606/106, 138, 97–100, 205–207, 96
See application file for complete search history.

(56) References Cited

U.S. PATENT DOCUMENTS

| | | | | |
|---|---|---|---|---|
| 3,478,435 A | * | 11/1969 | Cook | 33/511 |
| 4,270,274 A | * | 6/1981 | Hennessy | 33/511 |
| 4,352,245 A | * | 10/1982 | Hennessy et al. | 33/511 |
| 4,519,144 A | * | 5/1985 | Larsen | 33/199 R |
| 4,815,218 A | * | 3/1989 | Gordy | 33/628 |
| 4,821,587 A | * | 4/1989 | Rogers | 73/864.63 |
| 4,858,330 A | * | 8/1989 | Larsen | 33/199 R |
| 5,013,318 A | | 5/1991 | Spranza, III | |
| 5,191,719 A | * | 3/1993 | Kitt | 33/719 |
| 5,242,448 A | | 9/1993 | Pettine et al. | |
| 5,497,560 A | * | 3/1996 | Pasquerella et al. | 33/836 |
| 5,697,163 A | * | 12/1997 | Ulrich | 33/511 |
| 5,885,293 A | * | 3/1999 | McDevitt | 606/80 |
| 5,928,243 A | | 7/1999 | Guyer | |
| 6,427,351 B1 | * | 8/2002 | Matthews et al. | 33/512 |
| 6,450,976 B1 | * | 9/2002 | Korotko et al. | 600/587 |
| 6,761,726 B1 | * | 7/2004 | Findlay et al. | 606/182 |
| 6,764,453 B1 | * | 7/2004 | Meier | 600/587 |
| 2005/0027215 A1 | * | 2/2005 | Baxter-Jones et al. | 600/591 |

* cited by examiner

*Primary Examiner*—Yaritza Guadalupe-McCall
(74) *Attorney, Agent, or Firm*—Jones Day (57) ABSTRACT

A device for taking length and depth measurements during surgery. The device comprises a first longitudinal member and a second longitudinal member telescopically positioned within the first longitudinal member. The second longitudinal member may have a front part connectable thereto. The front part may have an opening, a passageway, and a moveable piece in the passageway. The device may also have a sliding member for moving the moveable piece between a first position where a portion of the moveable piece is outside the front part to a second position where the entire moveable piece is within the front part. The first and second longitudinal member may be locked with respect to one another. The prevent invention also discloses methods of using the device to take length and depth measurements during surgery.

64 Claims, 6 Drawing Sheets

DEVICE FOR LENGTH AND DEPTH MEASUREMENTS IN SURGERY

CROSS REFERENCE TO RELATED APPLICATION

The present application is a continuation of International Patent Application PCT/CH02/00071 filed Feb. 7, 2002, the entire content of which is expressly incorporated herein by reference thereto.

FIELD OF THE INVENTION

The invention relates to a device for length and depth measurements in surgery and, in particular, a device for positioning through a borehole in a bone to measure the distance from one side of the bone to the other side of the bone.

BACKGROUND OF THE INVENTION

Bone screws are commonly used in osteosynthetic repair of, for example, bone fractures. Frequently, bone screws are screwed into a bone perpendicular to its longitudinal axis. In so doing, the bone screws may penetrate into an opposite bone wall. However, the tip of the screw should not protrude excessively into the surrounding soft-tissue for this may result in irritation of or damage to the soft parts. An accurate determination of length of the borehole is therefore important for choosing the bone screw, which is to be inserted into a pre-drilled borehole.

In previously known devices for measuring length or depth, a piston with a hook was introduced through a borehole and engaged an opposite bone wall on the soft-tissue side. Subsequently, a measuring sleeve was shifted on the piston in the direction of the bone surface until the front end of the measuring sleeve came into contact with this surface. However, in so doing, the danger exists that the hook may slip off the opposite bone wall and, consequently, the displacement of the measuring sleeve may pull the hook into the bone. This may result in incorrect length measurements and, consequently, may result in the selection of a bone screw of the incorrect length.

The invention solves this problem and is designed to provide a length or depth measurement device, which enables a hook to extend beyond the opposite bone wall after the piston is moved into the borehole so that a positive connection to the bone can be achieved. Moreover, reading the length measurement does not have to occur in situ.

SUMMARY OF THE INVENTION

The present invention comprises two telescopic parts disposed coaxially with a longitudinal axis. The first part may be constructed as a measuring piston and the second part may be constructed as a measuring sleeve. The measuring piston may be moved axially in a central borehole of the measuring sleeve and its front part may be inserted into a borehole in a bone. The measuring piston may have a tip at its front part, and may also comprise a movable arresting means, which may be disposed movably within the measuring piston, and a hook, which may be extended and retracted at the tip in a direction transverse to the longitudinal axis.

In order to take measurements, the measuring piston may be inserted into a borehole in a bone while the measuring sleeve is in a retracted position and pushed therethrough until the tip protrudes beyond the opposing bone wall. Subsequently, the hook at the tip may be moved out of the front part. With the hook extended, the measuring piston may no longer be pulled out of the borehole and the device, as a whole, may no longer be withdrawn from the bone. Thereafter, the measuring sleeve may be moved on the measuring piston in the direction of the bone surface, until the front end of the measuring sleeve rests on the bone surface. At the same time, the bone may be clamped between the extended hook and the measuring sleeve. Finally, the hook may be retracted once again in a direction transverse to the longitudinal axis of the measuring piston, and the device may be pulled out of the borehole in the bone and removed from the field of the surgery.

In a preferred embodiment of the inventive device, the measuring sleeve and the measuring piston may comprise locking means. The locking means may hold the measuring piston in a selected position relative to the measuring sleeve, so that the device may be removed from the bone and the length measurement may be read outside of the surgical field. This allows for easy reading of the length measurement outside of the surgical field. The operating surgeon may freely hold the device such that neither light reflection off the device nor the style/font of the measurement markings affect the surgeon's measurement readings.

The advantages achieved by the present invention are apparent in that due to the present invention:
- when the hook is extended, the measuring piston may be prevented from slipping off an opposite bone wall;
- any unintentional movement of the measuring piston relative to the measuring sleeve may be prevented by a locking means, which may be disposed between the measuring piston and the measuring sleeve, and
- the length measurement may not have to be read in situ and, thus, good readability may be achieved.

In a further embodiment of the present invention, the arresting means may comprise a sliding element with an arresting mechanism, which may be moved coaxially with the longitudinal axis. At the front end of the sliding element, a rod having a wire may be mounted coaxially, with the wire forming an extended or retracted hook depending on the axial position of the sliding element. A curved or angled central borehole in the front part of the first part may result in the bending of the hook. The sliding element may be locked and unlocked by the arresting mechanism.

In yet another embodiment of the present invention, the arresting means may comprise a screw, which may be rotated into or out of the first part parallel to the longitudinal axis. A rod with a wire may be mounted so that it is rotatable but not axially moveable about the longitudinal axis and coaxial with the longitudinal axis at the front end of the screw. Similar to the embodiment described above, the wire may form the extended or retracted hook depending on the axial position of the screw. In another embodiment, an arresting mechanism, similar to those used as part of a conventional commercial ballpoint pen, may be used along with a wire to form the hook at the tip of the first part.

Further advantageous developments of the present invention are discussed in the further detail below.

BRIEF DESCRIPTION OF THE DRAWINGS

The invention and further developments of the invention are explained in even greater detail in the following exemplary drawings. The present invention can be better understood by reference to the following drawings, wherein like references numerals represent like elements. The drawings are merely exemplary to illustrate certain features that may

DETAILED DESCRIPTION

Figure 1:
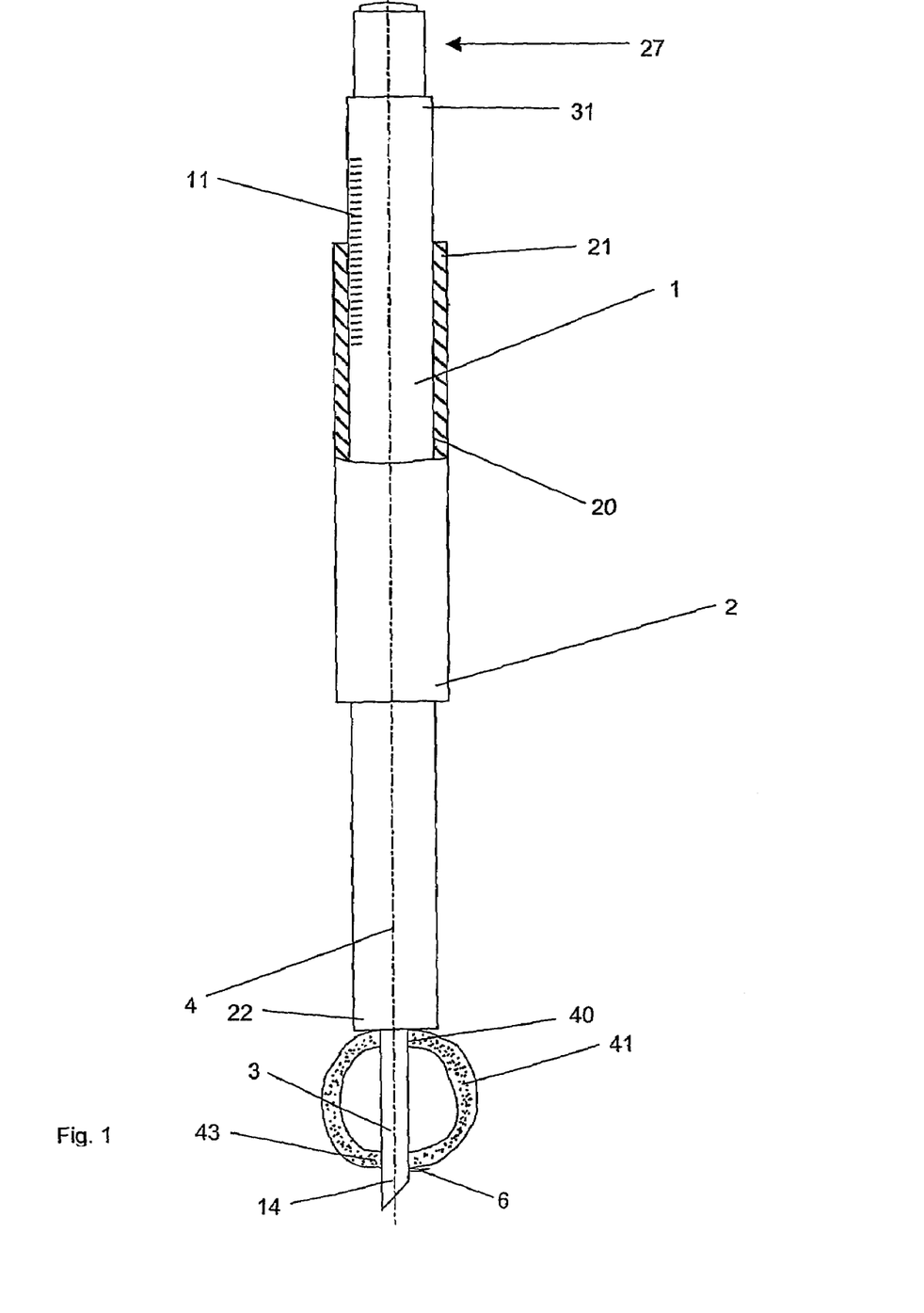
FIG. 1 is a partial cross-sectional view of an embodiment of the device of the present invention.

As shown in FIG. 1, the present invention comprises a first part 1 and a second part 2, the first 1 part may be constructed as a measuring piston and the second part 2 may be constructed as a measuring sleeve. It should, however, be understood that those of ordinary skill in the art will recognize many modifications and substitutions which may be made to various elements of the present invention.

The first part 1 may be moved parallel to the longitudinal axis 4 within a central borehole 20 in the second part 2. Depending on the position of the first part 1 relative to the second part 2, the tip 14 of the front part 3 of the first part 1 may protrude beyond the front end 22 of the second part 2. The front part 3 may be introduced into a borehole 40 in a bone 41, until the tip 14 protrudes beyond the bone portion 43 of the bone 41. The arresting means 27 may be disposed within the first part 1 so that it may be displaced parallel to the longitudinal axis 4. A hook 6 may be connected with the arresting means 27 and may be extended from or retracted into the front part 3 transversely to the longitudinal axis 4, such that the front part 3 may no longer be pulled out of the borehole 40 in the bone 41. Furthermore, a scale 11 may be mounted on the first part 1, so that the length to be measured may be read on the scale 11 at the rear end 21 of the second part 2.

Figure 2:
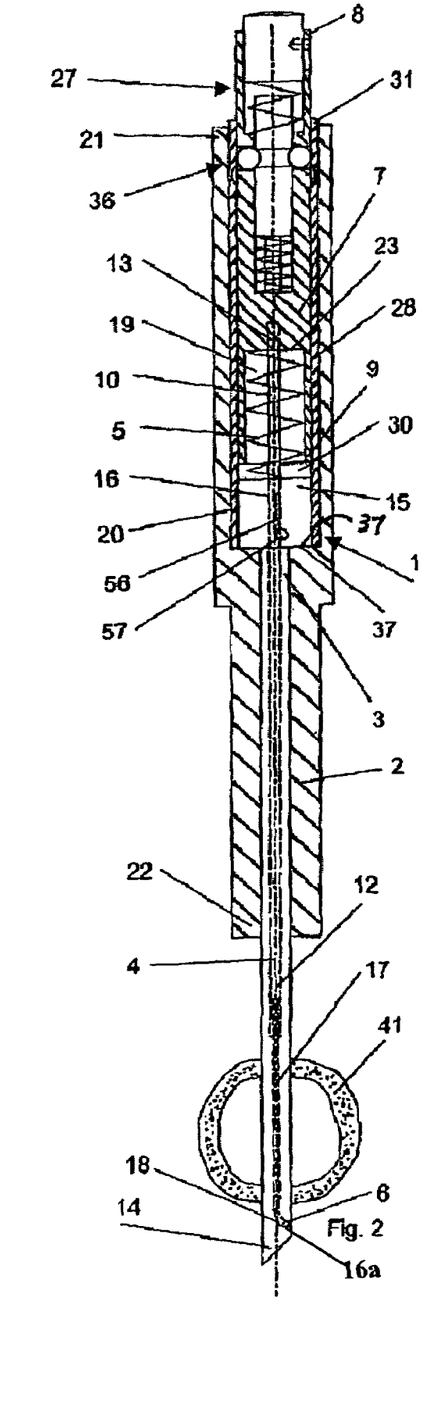
FIG. 2 is a cross-sectional view of an embodiment of the device of the present invention with a retracted hook.

FIG. 2 illustrates the first part 1 with the front part 3 and a sleeve 28, the sleeve 28 may be connected with the rear end 15 of the front part 3 and may extend up to the rear end 31 of the first part 1. The front part 3 may have a passage (such as borehole 16) therethrough which may extend from the rear end 15 to the tip 14. The borehole 16 may be angled or curved at the tip 14 by means of a curvature 18 or an offset angle such that the outlet or opening 16a of the borehole 16 at the tip 14 may extend in a direction transverse to the longitudinal axis 4. From the curvature 18, the borehole 16 may extend to the rear end 15 coaxially with the longitudinal axis 4. A sliding element 7 may be inserted into a central borehole 30 of the sleeve 28 so that it may be moved parallel to the longitudinal axis 4. The sliding element 7 may have a rear end 8, which may protrude beyond the rear end 31 of the first part 1, and a front end 9, which may contact the rear end 15 of the front part 3.

A rod 10 may be connected at a rear end 13 to the sliding element 7 and may extend coaxially with the longitudinal axis 4 from the front end 9 of the sliding element 7 through the borehole 16 in the front part 3. The rod 10 may also have a wire 17 at a front end 12. The wire 17, which may also be coaxial with the longitudinal axis 4, may extend from the front part 12 of the rod 10 through the opening 16a of the borehole 16 in the front part 3. The wire 17 may be bent in a direction transverse to the longitudinal axis 4 by the curvature 18 of the tip 14, thereby forming a hook.

In FIG. 2, the sliding element 7 is shown in its rear position. In this rear position, the rod 10 and the wire 17 may be retracted into the borehole 16 towards the rear end 15 of the front part 3, thus moving the hook 6 into the front part 3. The sliding element 7 may be retracted with a return spring 5, which may be positioned within a cavity 19 in the sliding element 7 and which may extend parallel to the longitudinal axis 4 from the front end 9 of the sliding element 7 to a position 23. One end of the return spring 5 may be in contact with a portion of the cavity at the position 23 and the other may be in contact with the rear end 15 of the front part 3. In addition to the sliding element 7, the rod 10 and the wire 17, the arresting means 27 may comprise an arresting mechanism 36, which is in an inactive position when the hook 6 is retracted.

FIG. 2 illustrates the present invention in a position prior to measuring a length or a depth. In this position, the second part 2 may be furthest to the rear—that is, the rear end 21 of the second part 2 may be proximate the rear end 31 of the first part 1. A shoulder 37 in the central borehole 20 of the second part 2 may provide a stopping surface for this furthest rearward position. And, the sleeve 28 and the rear end 15 of the front part 3 may abut the shoulder 37.

Figure 3:
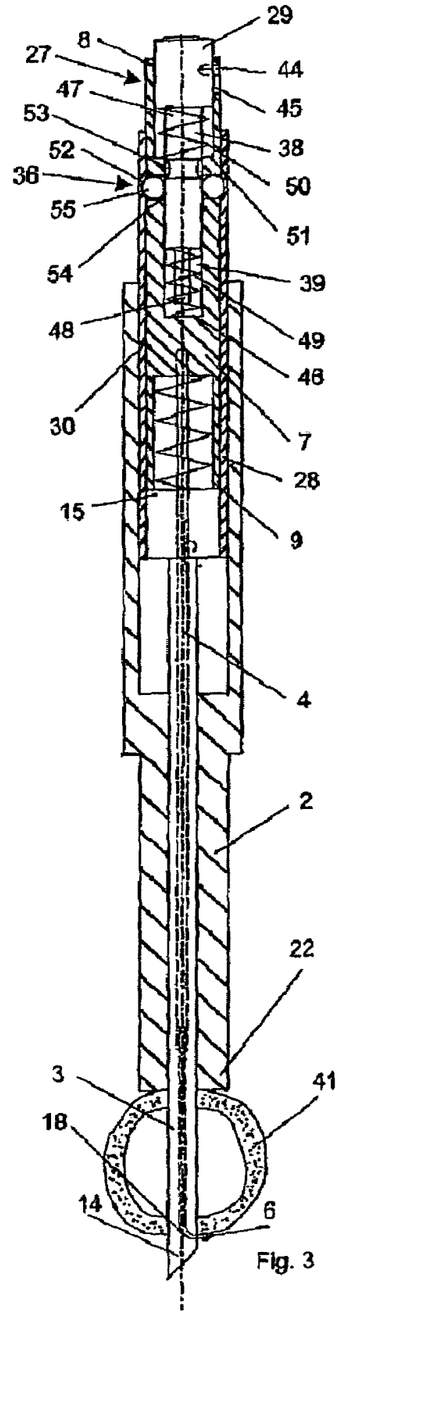
FIG. 3 is a cross-sectional view of the embodiment of the device of FIG. 2 with the an extended hook.

FIG. 3 shows a position of the arresting means 27 in which the hook 6 is in its extended position. In order to achieve this position, the sliding element 7 may be moved forward in the sleeve 28 until the front end 9 of the sliding element 7 abuts the rear end 15 of the front part 3. In this position, the arresting mechanism 36 may be in its active position (i.e., the hook 6 may be fixed in an extended position).

The sliding element 7 may have a hole 39 coaxial with the longitudinal axis 4 and opened at the rear end 8 of the sliding element 7. The arresting mechanism 36 may comprise a piston 38, which may be axially displaceable and which may be positioned in a hole 39. Bottom 46 may form a boundary of the hole 39 at a particular depth within sliding element 7. The piston 38 may be moved manually by an operating means 29—that is, moved towards the front end 9 of the sliding element 7. The operating means 29 may protrude beyond the rear end 8 of the sliding element 7. The path of travel of the operating means 29 parallel to the longitudinal axis 4 may be controlled by a pin 44, which may be guided in an elongated slot 45 in the wall of the sliding element 7.

To move the piston 38, the operating means 29 may be moved towards the tip 14 until the operating means 29 contact the rear end 47 of the piston 38 and subsequently moves the piston 38 towards the tip 14. The path of travel of the piston 38 towards the tip 14 may be limited by the front end 48 of the piston 38 contacting the bottom 46 of the blind hole 39 (FIG. 2). The piston 38 may be biased into a rear position by a first spring 49 which, at one end, may abut the piston 38 and, at another end, may abut the bottom 46 of the hole 39. The operating means 29 may also be brought into a rear position by a second spring 50. The second spring 50 may also be disposed in the hole 39 with one end of the spring contacting a shoulder 51 in the hole 39 and the other end of the spring contacting the operating means 29.

The arresting means 36 may be moved into two positions—an active position (FIG. 3), in which the sliding element 7 may be fixed in a forward position and the hook 6 may be fixed in an extended position, and an inactive position (FIG. 3), in which the arresting mechanism 36 may not engage the sliding element 7 and the hook 6 may be fixed in a retracted position. The sliding element 7 may be held in a forward position by balls 55, which may snap into a first groove 52 located in the periphery of the central borehole 30 of the sleeve 28 (FIG. 3). The balls 55 may be moved transverse to the longitudinal axis 4 and may be supported in transverse boreholes 54, which may pass diametrically through the sliding element 7. In the active position of the arresting mechanism 36 (FIG. 3), the balls 55 may be held by the piston 38. In the inactive position of the arresting mechanism 36 (i.e., when the slide element 7 is in its rear position) the balls 55 may snap into a second groove 53, which may be located on the periphery of the piston 38. Accordingly, the sliding element 7 may be pushed towards its rear position by the force of the return spring 5 (FIG. 2) or towards its front position relative to the sleeve 28.

The sliding element 7 may be held in its rear position by a pin 57, which may be mounted transversely to the longitudinal axis 4 at the rear end 15 of the front part 3 and which may be received within a notch 56 of the rod 10, so that movement of the sliding element 7 parallel to the longitudinal axis 4 and towards the rear end 31 of the sleeve 28 may be limited by the notch 56.

Figure 5:
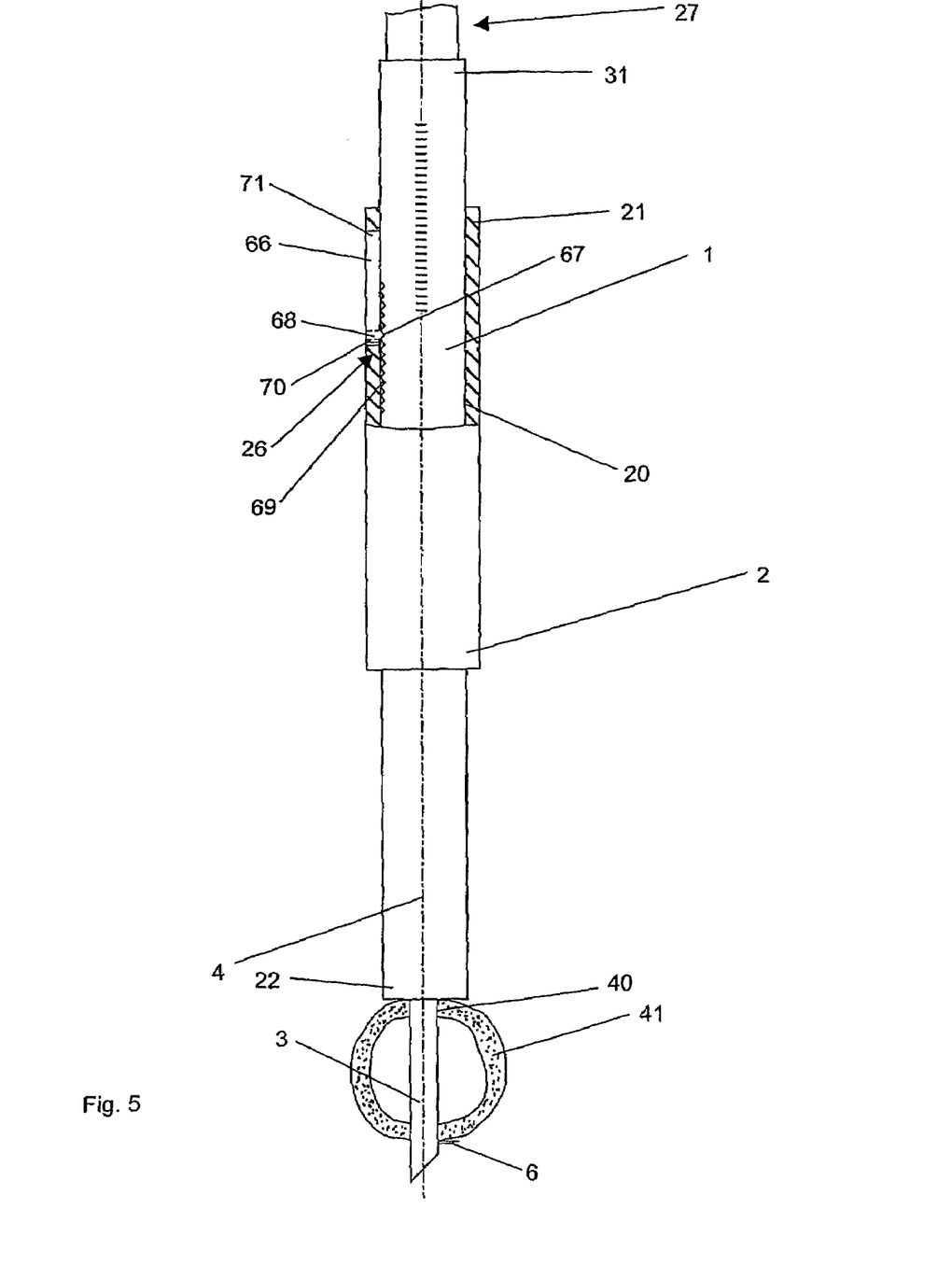
FIG. 5 is a partial cross-sectional view of another alternative embodiment of the device of the present invention.
Figure 6:
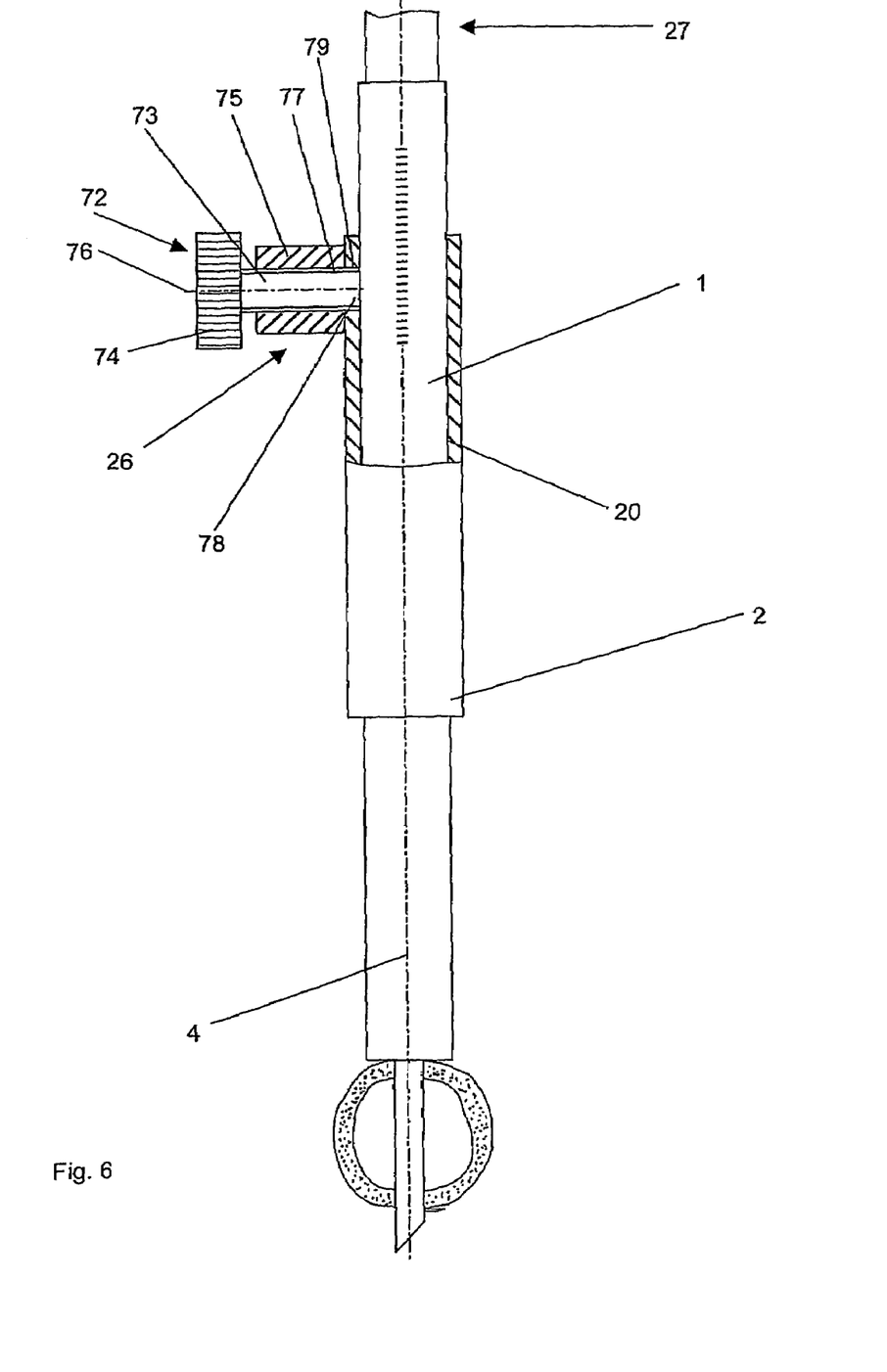
FIG. 6 is a partial cross-sectional view of yet another alternative embodiment of the device of the present invention.
Figure 7:
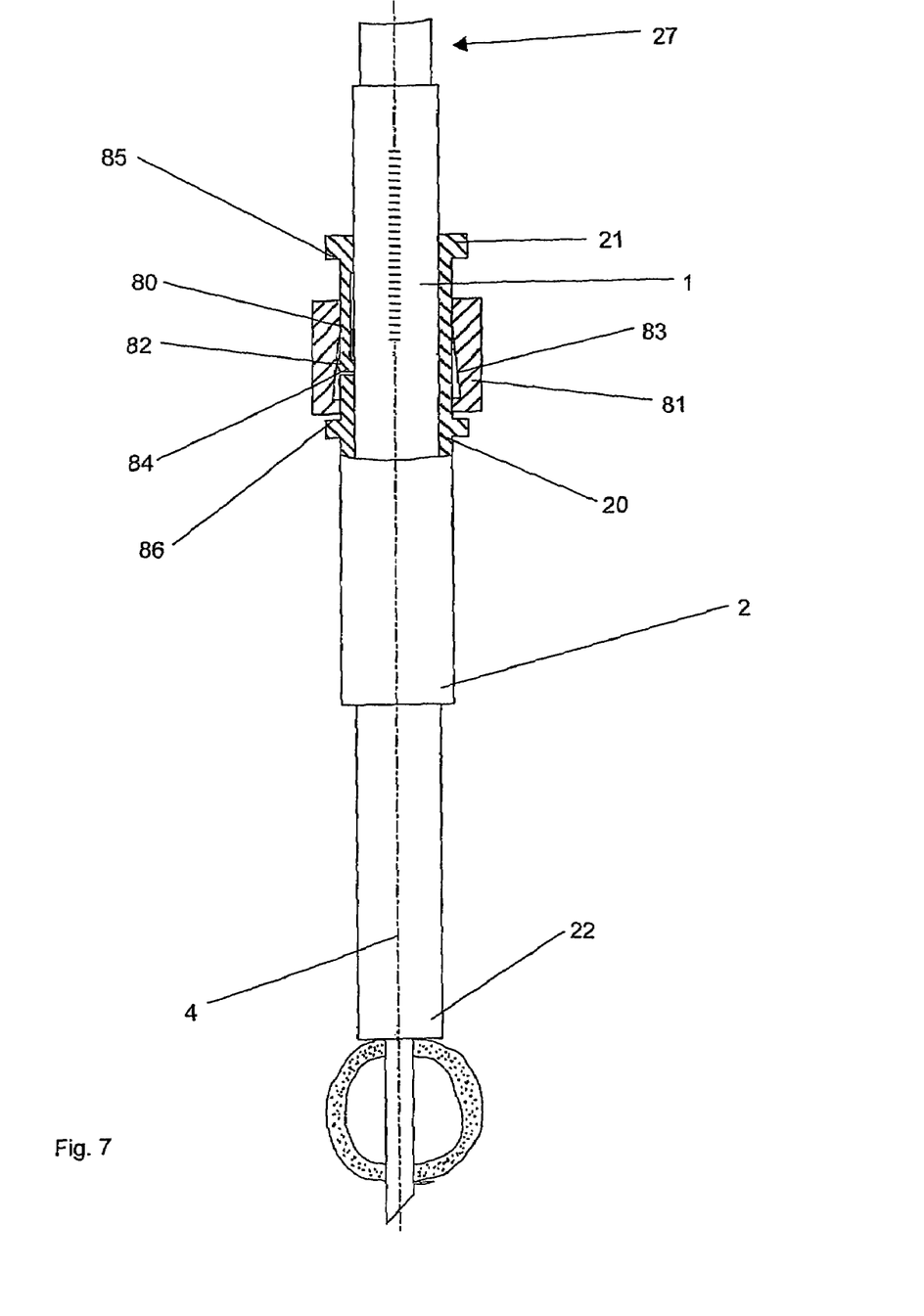
FIG. 7 is a partial cross-sectional view of another embodiment of the device of the present invention.

FIGS. 1 to 3 illustrate the present invention in use, for example, while taking the length measurement of a hole in a bone which will receive a bone screw to be screwed into a bone 41. In order to measure length, the front part 3 of the first part 1 may be inserted into the borehole 40 in the bone 41 until the tip 14 protrudes beyond the opposite bone wall 43. At this point, the rear end 21 of the second part 2 may be positioned adjacent the rear end 31 of the first part 1 (i.e., rear end 21 may be positioned furthest to the rear (FIG. 2)). Next, the hook 6 of the arresting means 27 may be extended using the operating means 29, which may be disposed at the rear end 31 of the first part 1, and may be fixed in an extended position. Subsequently, the second part 2 may be moved forward (i.e., in a direction towards the front part 3) until the front end 22 of the second part 2 is in contact with the surface of the bone 41 (FIG. 3). At this point, the bone 41 may be clamped between the front end 22 of the second part 2 and the hook 6. The second part 2 may be held in position relative to the first part 1 by a locking means 26 (FIGS. 5 through 7). The hook 6 of the arresting means 37 may then be retracted by manipulating the operating means 29 and the device may be removed from the borehole 40 in the bone 41. The length measured may be subsequently read from the scale 11 (FIG. 1) in the operating room outside of the field of surgery.

Figure 4:
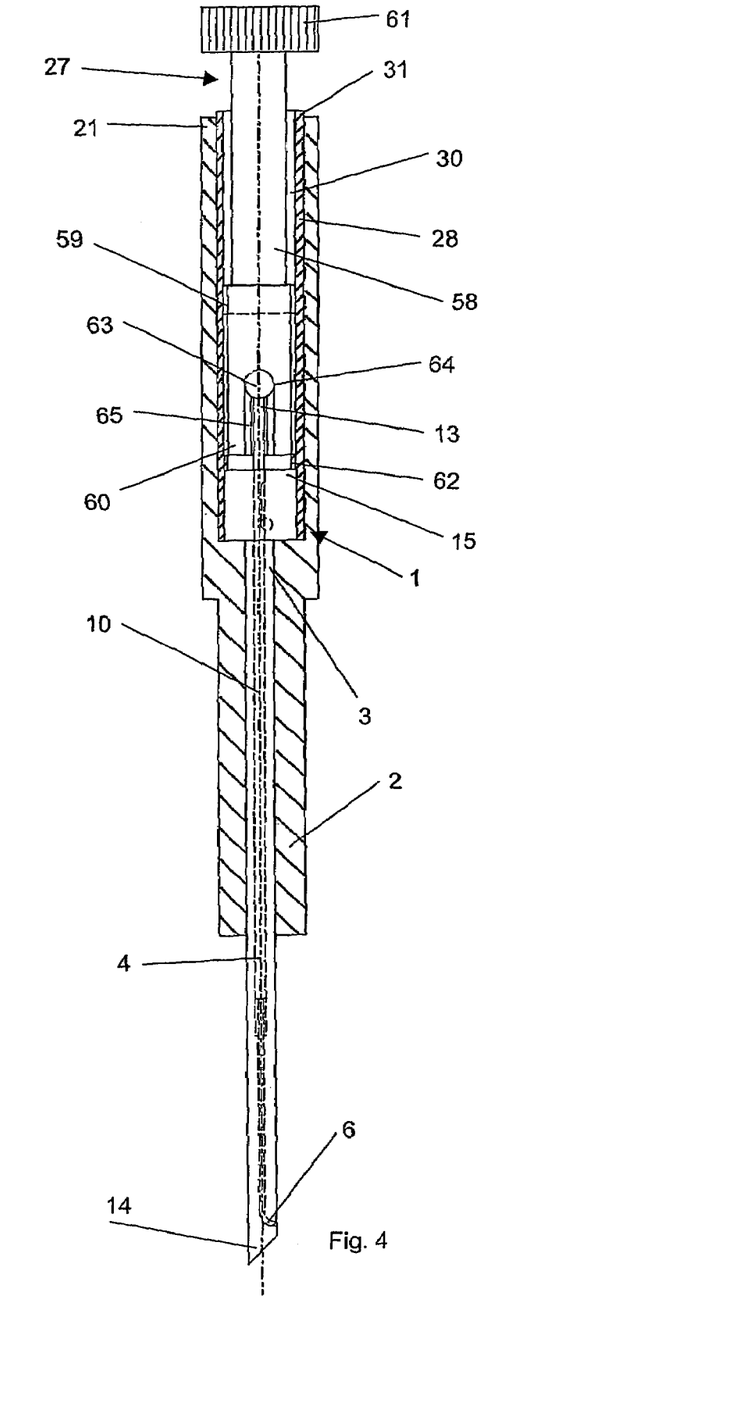
FIG. 4 is a cross-sectional view of an another embodiment of the device of the present invention.

The embodiment illustrated in FIG. 4 differs from the embodiments of FIGS. 2 and 3 in that the arresting means 27 may comprise a screw 58 instead of the sliding element 7 of FIGS. 2 and 3. The rear end 61 of the screw 58 may protrude over the rear end 21 of the first part 1 and may be rotated manually. The screw 58 may be provided with an external thread extending along its front part to a front end 60. The external thread 59 may be screwed into an internal thread 62 of the first part 1. The internal thread 62 may be positioned in the central borehole 30 of the sleeve 28 and may extend up to the rear end 15 of the front part 3. Accordingly, the screw 58 may be screwed into the first part 1 until the front end 60 of the screw 58 contacts the rear end 15 of the front part 3. The hook 6 may be in a retracted position when the screw 58 is in a rear position. Otherwise, when the screw 58 is in a forward position (i.e., where the screw 58 is positioned so far into the first part 1 that the front end 60 of the screw 58 contacts the rear end 15 of the front part 3), the hook 6 may be fixed in an extended position. The hook 6 may be fixed in this position by the threaded connection between the first part 1 and the screw 58.

The rear end 13 of the rod 10 may have a spherical head 63. The rear end 13 having spherical head 63 may be positioned in a hole 64, which may be located in the screw 58. The hole 64 may extend coaxially with the longitudinal axis 4 and may be open at the front end 60 of the screw 58. The spherical head 63 may be fixed axially against the front end 60 of the screw 58, for example, by an insert 65 in the hole 64. Therefore, the rod 10 may be fixed axially but may be connected to the screw 58 so that the rod 10 may freely rotated about the longitudinal axis 4.

FIGS. 5 through 7 of the present invention illustrate one embodiment of FIGS. 1 through 4 with locking means 26 for selectively locking the relative axial position between the first part 1 and the second part 2.

FIG. 5 shows an embodiment of the present invention where the locking means 28 may comprise a flexible flap 68, which may be flexible in a direction transverse to the longitudinal axis 4, and teeth 69, which may be mounted on the first part 1 parallel to the longitudinal axis 4. A rigid end 71 of the flexible flap 66 may be fastened to the second part 2 proximate the rear end 21 of the second part 2. The flexible flap 66 may be provided at its free end 70 with a protrusion 67, which may extend towards the central borehole 20 of the second part 2. The protrusion 67 may engage the teeth 69 so that the first part 1 may be fixed against axially movement with respect to the second part 2. The teeth 69 may have, for example, notches at millimeter intervals so that the first part 1 may be fixed in millimeter intervals relative to the second part 2. The protrusion 67 may be formed, for example, by a pin 68 whose tip engages the teeth 69.

FIG. 6 shows an embodiment of the present invention where the locking means 21 may comprise a fixing screw 72 having a screw axis 78 extending in a direction transverse to the longitudinal axis 4. The shaft 73 of the fixing screw 72 may be passed through a borehole 79 in the second part 2 and screwed into an internal thread 77 of a bushing 75. In this way, the front end 78 of the fixing screw 72 may extend into the central borehole 20 of the second part 2 and may be pressed against the first part 1. The bushing 75 may be fastened to the second part 2. The head 74 of the fixing screw 72 may extend out over the bushing 75 and may be rotated manually so that the first part 1 and the second part 2 may be locked together by tightening the fixing screw 72. The internal thread 77 may also be provided in the borehole 79 of the second part 2 if the wall of the second part 2 between the outer surface and the central borehole 20 is sufficiently thick.

FIG. 7 shows an embodiment of the present invention where the locking means 26 may comprise a flap 80 connected with the second part 2, which may be elastically deformed and which may move in a direction transverse to the longitudinal axis 4. A clamping sleeve 81, which may be moved on the second part 2 parallel to the longitudinal axis 4, may be used to press the flap 80 laterally against the first part 1 so that the first part 1 may be fixed relative to the second part 2. In order to loosen or tighten the locking means 26, the elastically deformable end 84 of the flap 80 may have a protrusion 82 adjacent the wall of the inner cone 83. The inner cone 83 may taper towards the rear end 21 of the second part 2 and may be provided in the clamping sleeve 81. If the clamping sleeve 81 is moved towards the front end 22 of the second part 2, the inner cone 83 may press against the protrusion 82 and, thus, the flap 80 may be pressed laterally against the first part 1. To loosen the locking means 26, the clamping sleeve 81 may be moved axially towards the rear end 21 of the second part 2 until the inner cone 83 disengages the protrusion 82. The axial movement of the clamping sleeve 81 towards the rear end 21 of the second part 2 may be limited by a first stop 85 at the rear end 21 of the second part 2 and axial movement towards the front end 22 of the second part 2 may be limited by a second stop 86.

After the front end of the second part 2 is brought into contact with the surface of the bone 41, the second part 2 may be held in position relative to the first part 1 by the locking means 26. Thus, after the hook 6 of the arresting means 27 is retracted, the device may be pulled out of the borehole 40 in the bone 41 without moving the axial position of the first part 1 relative to that of the second part 2, which would otherwise be able to move.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A device for measuring a distance from a first side of a tissue to a second side of the tissue comprising:
    a first longitudinal member having a longitudinal axis and a front end, wherein the front end is positionable against the first side of the tissue;
    a second longitudinal member, the second longitudinal member being moveable along the longitudinal axis of the first longitudinal member;
    a front part operatively associated with the second longitudinal member, the front part having an opening, a passageway therethrough, and a moveable piece in the passageway; and
    a sliding member operatively connectable to the moveable piece for moving the moveable piece between a first position where a portion of the moveable piece is outside the front part to a second position where the entire moveable piece is within the front part, wherein the sliding member is capable of moving independently of the second longitudinal member, and wherein in the first position the moveable piece is positionable against the second side of the tissue.

2. The device of claim 1 further comprising a locking mechanism for fixing the first longitudinal member relative to the second longitudinal member.

3. The device of claim 2, wherein the locking mechanism comprises:
    a flexible arm operatively connectable to the first longitudinal member, the flexible arm having at least one protrusion; and
    teeth extending along a portion of the second longitudinal member;
    wherein the at least one protrusion engages the teeth of the second longitudinal member.

4. The device of claim 2, wherein the locking mechanism comprises:
    a screw; and
    a receiving portion operatively connectable to the first longitudinal member, the receiving portion and the first longitudinal member having an opening passing therethrough;
    wherein the screw is positioned through the opening of the receiving portion and the first longitudinal member and engages the second longitudinal member.

5. The device of claim 2, wherein the locking mechanism comprises:
    a flexible member operatively connectable to the first longitudinal member, the flexible member having a protrusion; and
    a sleeve positioned around the flexible member, the sleeve having a first position and a second position;
    wherein moving the sleeve to the first position causes the protrusion of the flexible member to contact the second longitudinal member thereby fixing the first longitudinal member relative to the second longitudinal member, and wherein moving the sleeve to the second position allows the protrusion of the flexible member to be disengaged from the second longitudinal member such that the first longitudinal member is free to move with respect to the second longitudinal member.

6. The device of claim 5, wherein the locking mechanism further comprises at least one stopping portion.

7. The device of claim 1, wherein the second longitudinal member comprises markings.

8. The device of claim 1, wherein the moveable piece is a wire.

9. The device of claim 1 wherein the front part has a longitudinal axis, wherein the passageway of the front part has a curved portion such that the moveable piece is moved out of the front part in a direction transverse to the longitudinal axis of the front part.

10. The device of claim 1, wherein the sliding member comprises:
    a slidable portion axially moveable in a direction parallel to the longitudinal axis;
    a rod having a first end and a second end, the first end operatively connected to the slidable portion and the second end operatively connected to the moveable piece; and
    an actuator for selectively locking and unlocking the position of the slidable portion relative to the second longitudinal member.

11. The device of claim 10 further comprising a biasing means, the biasing means being positioned between the front part and the slidable portion, wherein the biasing means biases the slidable portion away from the front part.

12. The device of claim 11, wherein the biasing means is a spring.

13. The device of claim 11, wherein the front part comprises a pin and the rod comprises a notch, the notch being moveable along the pin and limiting the movement of the slidable portion away from the front part.

14. The device of claim 10, further comprising at least one indent within the second longitudinal member.

15. The device of claim 14, wherein the actuator comprises:
    an operating piece;

a piston having a top portion, a bottom portion and a ball receiving portion; and at least one ball, the at least on ball being received within the ball receiving portion of the piston;

wherein the bottom portion of the piston contacts the slidable portion and pushing the operating piece into contact with the top portion of the piston moves the piston and the slidable portion towards the front part, and wherein the at least one ball engages the at least one indent as the piston is moved toward the front part.

16. The device of claim 15, wherein the sliding member comprises a wall having a slot therethrough.

17. The device of claim 16, wherein the operating piece comprises a protrusion, the protrusion being receiving in the slot in the wall of the sliding member and being axially moveable therein.

18. The device of claim 15, wherein the actuator further comprises a first spring, the first spring biasing the operating piece away from the top portion of the piston.

19. The device of claim 18, wherein the actuator further comprises a second spring positioned around the piston, the second spring biasing the bottom portion of the piston away from the slidable portion.

20. The device of claim 15, wherein the at least one ball moves out of the ball receiving portion and is positioned between the at least one indent and the piston, thereby holding the slidable portion adjacent the front part.

21. The device of claim 1, wherein the front part has a longitudinal axis, the passageway extending substantially along the longitudinal axis of the front part and the opening being in communication with the passageway but not aligned with the longitudinal axis of the front part.

22. The device of claim 21, wherein the front part has a side portion, the opening is positioned through the side portion.

23. The device of claim 21, wherein a portion of the passageway is transverse to the longitudinal axis of the front part.

24. The device of claim 1, wherein the front part has a longitudinal axis, at least a portion of the passageway being curved.

25. The device of claim 1, wherein the passageway has a proximal end and a distal end, the distal end having a curved shape.

26. The device of claim 1, wherein the moveable piece is configured to bend as the moveable piece moves through the passageway.

27. A device for measuring a distance between a first side of a tissue and a second side of the tissue comprising:

a first longitudinal member having a front end, wherein the front end is positionable against the first side of the tissue;

a second longitudinal member, the second longitudinal member being slidably moveable relative to the first longitudinal member;

a front part operatively connected to the second longitudinal member, the front part having an opening, a passageway therethrough, and a moveable piece in the passageway, wherein the moveable piece is positionable against the second side of the tissue;

a sliding member operatively associated with the moveable piece for moving the moveable piece between a first position and a second position, wherein the sliding member is capable of moving independently of the second longitudinal member; and a locking mechanism for fixing the first longitudinal member relative to the second longitudinal member.

28. The device of claim 27, wherein the locking mechanism comprises:

a flexible arm operatively connected to the first longitudinal member, the flexible arm having at least one protrusion; and teeth extending along a portion of the second longitudinal member;

wherein the at least one protrusion engages the teeth of the second longitudinal member.

29. The device of claim 27, wherein the locking mechanism comprises:

a screw; and a receiving portion operatively connected to the first longitudinal member, the receiving portion and the first longitudinal member having an opening passing therethrough;

wherein the screw is positioned through the opening of the receiving portion and the first longitudinal member and engages the second longitudinal member.

30. The device of claim 27, wherein the locking mechanism comprises:

a flexible member operatively connected to the first longitudinal member, the flexible member having a protrusion; and a sleeve positioned around the flexible member, the sleeve having a first position and a second position;

wherein moving the sleeve to the first position causes the protrusion of the flexible member to contact the second longitudinal member thereby fixing the first longitudinal member relative to the second longitudinal member, and wherein moving the sleeve to the second position allows the protrusion of the flexible member to be disengaged from the second longitudinal member such that the first longitudinal member is free to move with respect to the second longitudinal member.

31. The device of claim 30, wherein the locking mechanism further comprises at least one stopping portion.

32. The device of claim 27, wherein the second longitudinal member comprises markings.

33. The device of claim 27, wherein the moveable piece is a wire.

34. The device of claim 27 wherein the first part has a longitudinal axis, wherein the passageway of the front part has a curved portion such that the moveable piece is moved out of the front part in a direction transverse to the longitudinal axis of the first part.

35. The device of claim 27 further comprising a longitudinal axis, wherein the sliding member comprises:

a slidable portion axially moveable in a direction parallel to the longitudinal axis;

a rod having a first end and a second end, the first end operatively connected to the slidable portion and the second end operatively connected to the moveable piece; and an actuator for selectively locking and unlocking the position of the slidable portion relative to the second longitudinal member.

36. The device of claim 35 further comprising a biasing means, wherein the biasing means biases the slidable portion away from the front part.

37. The device of claim 36, wherein the biasing means is a spring.

38. The device of claim 35, further comprising at least one indent within the second longitudinal member.

39. The device of claim 38, wherein the actuator comprises:

an operating piece;

a piston having a top portion, a bottom portion and a ball receiving portion; and
at least one ball, the at least one ball being received in the ball receiving portion of the piston;
wherein the bottom portion of the piston contacts the slidable portion and pushing the operating piece into contact with the top portion of the piston moves the piston and the slidable portion towards the front part, and wherein the at least one ball engages the at least one indent as the piston is moved toward the front part.

40. The device of claim 39, wherein the actuator further comprises a first spring, the first spring biasing the operating piece away from the piston.

41. The device of claim 40, wherein the actuator further comprises a second spring positioned around the piston, the second spring biasing the piston towards the operating piece.

42. The device of claim 39, wherein the at least one ball moves out of the ball receiving portion and is positioned between the at least one indent and the piston, thereby holding the slidable portion adjacent the front part.

43. A method of measuring a distance between a first side of a tissue and a second side of the tissue comprising:
providing a measuring device comprising:
a first longitudinal member having a front end;
a second longitudinal member, the second longitudinal member being telescopically moveable with respect to first longitudinal member;
a front part operatively connectable to the second longitudinal member, the front part having a moveable piece therein; and
a sliding member operatively connectable to the moveable piece for moving the moveable piece between a first position and a second position;
inserting the front part of the measuring device through the tissue;
extending the moveable piece of the measuring device out of the opening of the front part by actuating the sliding member;
positioning a portion of the extended moveable piece against the second side of the tissue; and
moving a portion of the front end of the first longitudinal member against the first side of the tissue so that the tissue is positioned between the moveable piece and the front end of the first longitudinal member.

44. The method of claim 43 further comprising the step of fixing the first longitudinal member with respect to the second longitudinal member.

45. The method of claim 44 wherein the second longitudinal member further comprises markings.

46. The method of claim 45 further comprising the steps of:
retracting the moveable piece into the opening of the front part;
removing the front part from the tissue; and
reading the marking on the second longitudinal member.

47. The method of claim 43 wherein the device further comprises a longitudinal axis and wherein the moveable piece extends out of the front part in a direction transverse to the longitudinal axis.

48. The method of claim 43 wherein the device further comprises at least one indent within the second longitudinal member.

49. The method of claim 48, wherein the sliding member comprise an actuator and a slidable portion positioned within the second longitudinal member, and wherein the actuator comprises:
an operating piece;
a piston having a ball receiving portion and engagable with the slidable portion; and
at least one ball, the at least one ball being received in the ball receiving portion of the piston.

50. The method of claim 49 further comprising the steps of:
pushing the operating piece into contact with the piston;
moving the slidable portion from a first position where the slidable portion is farther from the front part to a second position where the slidable portion is closer to the front part;
positioning the at least one ball within the at least one indent of the second longitudinal member; and
disengaging the at least one ball from the receiving portion of the piston;
wherein the at least one ball is held between the at least one indent of the second longitudinal member and the piston, thereby fixing the slidable portion in the second position.

51. The method of claim 49 further comprising the steps of:
pushing the operating piece and the piston towards the front part;
positioning the at least one ball within the receiving portion of the piston; and
disengaging the at least one ball from the at least one indent of the second longitudinal member;
wherein disengaging the at least one ball from the at least one indent enables the slidable portion to move to the first position.

52. A method of measuring a distance between a first side of a tissue and a second side of the tissue comprising:
providing a measuring device comprising:
a first longitudinal member having a front end;
a second longitudinal member, the second longitudinal member being telescopically received in the first longitudinal member, wherein the second longitudinal member comprises markings;
a front part operatively connectable to the second longitudinal member, the front part having a moveable piece therein; and
a sliding member operatively connectable to the moveable piece for moving the moveable piece between a first position and a second position;
inserting the front part of the measuring device through the tissue;
extending the moveable piece of the measuring device out of the opening of the front part by actuating the sliding member;
positioning a portion of the extended moveable piece against the second side of the tissue; and
moving a portion of the front end of the first longitudinal member against the first side of the tissue so that the tissue is positioned between the moveable piece and the front end of the first longitudinal member;
retracting the moveable piece into the opening of the front part;
removing the front part from the tissue; and
reading the marking on the second longitudinal member.

53. The method of claim 52 further comprising the step of fixing the first longitudinal member with respect to the second longitudinal member.

54. A device for measuring tissue comprising:
a first longitudinal member having a longitudinal axis and a front end;
a second longitudinal member, the second longitudinal member being moveable along the longitudinal axis of the first longitudinal member, wherein the second longitudinal member comprises an internal threaded portion;

a front part operatively associated with the second longitudinal member, the front part having an opening, a passageway therethrough, and a moveable piece in the passageway; and a sliding member operatively connectable to the moveable piece for moving the moveable piece between a first position where a portion of the moveable piece is outside the front part to a second position where the entire moveable piece is within the front part, wherein the sliding member is capable of moving independently of the second longitudinal member.

55. The device of claim 54 further comprising a longitudinal axis, wherein the sliding member comprises:

a screw having an external threaded portion and a rod receiving portion, the screw being axially moveable in a direction parallel to the longitudinal axis; and a rod having a first end and a second end, the first end operatively connectable to the rod receiving portion of the screw and the second end operatively connectable to the moveable member;

wherein the external threaded portion of the screw engages the internal threaded portion of the second longitudinal member such that rotation of the screw results in movement of the rod and the moveable member.

56. The device of claim 55, wherein the first end of the rod has a spherical shape and wherein the rod receiving portion engages the rod such that the rod moves axially with the axial movement of the screw but is prevented from moving rotationally as the screw is rotated.

57. The device of claim 56, further comprising a holding portion located between the first end of the rod and the front part, wherein the holding portion keeps the first end of the rod proximate the rod receiving portion.

58. A device for measuring tissue comprising:

a first longitudinal member having a front end;

a second longitudinal member, the second longitudinal member being slidably moveable relative to the first longitudinal member, wherein the second longitudinal member comprises an internal threaded portion;

a front part operatively connected to the second longitudinal member, the front part having an opening, a passageway therethrough, and a moveable piece in the passageway;

a sliding member operatively associated with the moveable piece for moving the moveable piece between a first position and a second position, wherein the sliding member is capable of moving independently of the second longitudinal member; and a locking mechanism for fixing the first longitudinal member relative to the second longitudinal member.

59. The device of claim 58 further comprising a longitudinal axis, wherein the sliding member comprises:

a screw having an external threaded portion and a rod receiving portion, the screw being axially moveable in a direction parallel to the longitudinal axis; and a rod having a first end and a second end, the first end operatively connected to the rod receiving portion of the screw and the second end operatively connected to the moveable member;

wherein the external threaded portion of the screw engages the internal threaded portion of the second longitudinal member such that rotation of the screw results in movement of the rod and the moveable member.

60. The device of claim 59, wherein the first end of the rod has a spherical shape and wherein the rod receiving portion engages the rod such that the rod moves axially with the axial movement of the screw but is prevented from moving rotationally as the screw is rotated.

61. The device of claim 60, further comprising a holding portion located between the first end of the rod and the front part, wherein the holding portion keeps the first end of the rod proximate the rod receiving portion.

62. A method of measuring tissue comprising:

providing a measuring device comprising:

a first longitudinal member having a front end;

a second longitudinal member, the second longitudinal member being telescopically moveable with respect to first longitudinal member;

a front part operatively connectable to the second longitudinal member, the front part having a moveable piece therein; and a sliding member operatively connectable to the moveable piece for moving the moveable piece between a first position and a second position, wherein the sliding member comprises a screw;

inserting the front part of the measuring device through the tissue;

extending the moveable piece of the measuring device out of the opening of the front part by actuating the sliding member; and moving the front end of the first longitudinal member towards the tissue so that the tissue is positioned between the moveable piece and the front end of the first longitudinal member, wherein the front end is capable of engaging the tissue.

63. The method of claim 62 further comprising the step of rotating the screw to move the moveable piece.

64. The method of claim 63, wherein the moveable piece is a wire.

* * * * *